United States Patent
Reif et al.

(10) Patent No.: US 6,900,348 B1
(45) Date of Patent: May 31, 2005

(54) LIGHT ISOCYANATES, METHOD FOR PRODUCING THEM AND USE THEREOF

(75) Inventors: Martin Reif, Ludwigshafen (DE); Peter van den Abeel, Brasschaat (BE); Filip Nevejans, Beveren-Waas (BE); Hans Volkmar Schwarz, Waterloo (BE); Ulrich Penzel, Tettau (DE); Volker Scharr, Senftenberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/018,636

(22) PCT Filed: Jun. 16, 2000

(86) PCT No.: PCT/EP00/05610

§ 371 (c)(1),
(2), (4) Date: Dec. 13, 2001

(87) PCT Pub. No.: WO01/00569

PCT Pub. Date: Jan. 4, 2001

(30) Foreign Application Priority Data

Jun. 23, 1999 (DE) .......................... 199 28 741

(51) Int. Cl.⁷ ............................................ C07C 263/00
(52) U.S. Cl. ....................................... 560/347
(58) Field of Search ................. 560/347, 330, 560/338

(56) References Cited

U.S. PATENT DOCUMENTS

| | | | |
|---|---|---|---|
| 3,660,261 A | | 5/1972 | Wright et al. |
| 3,916,006 A | * | 10/1975 | Schmitt et al. ............. 560/347 |
| 4,193,932 A | * | 3/1980 | Yamamoto et al. |
| 4,465,639 A | | 8/1984 | Hatfield |
| 4,774,357 A | | 9/1988 | Keggenhoff et al. |
| 5,207,942 A | | 5/1993 | Scherzer et al. |
| 5,208,368 A | | 5/1993 | Scherzer et al. |
| 5,364,958 A | | 11/1994 | Ishida et al. |
| 5,583,251 A | | 12/1996 | Buysch et al. |
| 5,872,278 A | | 2/1999 | Kraus et al. |
| 6,140,382 A | | 10/2000 | Gallus et al. |

FOREIGN PATENT DOCUMENTS

| | | |
|---|---|---|
| CA | 2038126 | 9/1991 |
| DE | 43 00 774 | 7/1994 |
| DE | 198 17 691 | 10/1999 |
| EP | 0 133 538 | 2/1985 |
| EP | 0 445 602 | 3/1990 |
| EP | 0 446 781 | 9/1991 |
| EP | 0 467 125 | 1/1992 |
| EP | 0 538 500 | 4/1993 |
| EP | 0 561 225 | 9/1993 |
| EP | 0 581 100 | 2/1994 |
| EP | 0 546 398 | 9/1996 |

OTHER PUBLICATIONS

International Preliminary Examination Report.

* cited by examiner

*Primary Examiner*—Paul A. Zucker
(74) *Attorney, Agent, or Firm*—Fernando A. Borrego; Howard & Howard Attys.

(57) ABSTRACT

A process is provided for preparing light-colored isocyanates which can be used for preparing urethane compounds, in particular polyurethanes, for example polyurethane foams.

18 Claims, No Drawings

LIGHT ISOCYANATES, METHOD FOR PRODUCING THEM AND USE THEREOF

This application is a 371 of PCT/EP00/05610 filed Jun. 16, 2000.

The present invention relates to light-colored isocyanates, a process for preparing light-colored isocyanates and also their use in urethane compounds, in particular in polyurethanes, for example in polyurethane foams.

Isocyanates and isocyanate mixtures are prepared by known methods by phosgenation of the corresponding amines. For polyurethane foams, use is made, for example, of bifunctional or polyfunctional aromatic isocyanates of the diphenylmethane diisocyanate series (MDI). Due to the preparation process, the phosgenation and subsequent work-up (removal of the solvent; separation of monomeric MDI) often results in dark-colored products which in turn give yellowish polyurethane foams or other, likewise discolored PUR materials. This is undesirable, since such discoloration adversely affects the overall visual impression and allows slight inhomogeneities to occur, e.g. as streaks in the foams obtained. Light-colored isocyanates or isocyanates which contain a reduced amount of color-imparting components are therefore preferred as raw materials.

There have always been many attempts to obtain polyisocyanates, in particular ones of the diphenylmethane diisocyanate series, having a light color. Numerous methods are known for empirically lightening the color of MDI. However, the nature of the troublesome colored substances has hitherto been elucidated only to an unsatisfactory degree.

The previously known methods can be divided into four groups:

1. Processes in which the starting material diaminodiphenylmethane (MDA) or its oligomers have been subjected to treatment and/or purification EP-A 0 546 398 describes a process for preparing polymeric MDI in which the polymethylene-polyphenylene-polyamine used as starting material is acidified prior to phosgenation.

EP-A 0 446 781 relates to a process for preparing polymeric MDA (monomeric and oligomeric polymethylene-polyphenylene-polyamines) which are firstly treated with hydrogen and subsequently subjected to a phosgenation, with a relatively light-colored MDI being obtained.

The abovementioned methods give only a slight improvement in the color, since the colored substances in the MDI have been found on the basis of experience to be formed not only from certain MDA secondary components but also to result from color precursors which are formed by secondary reactions during the phosgenation.

2. Process engineering solutions in the phosgenation process

U.S. Pat. No. 5,364,958 relates to a process for preparing polyisocyanates in which, after the phosgenation, the phosgene is removed completely at low temperature and the isocyanate is subsequently treated hot with HCl gas.

DE 19817691.0 describes a process for preparing MDI/PMDI mixtures having a reduced content of chlorinated by-products and a reduced iodine color number by adherence to defined parameters in the phosgenation reaction. In particular, adherence to particular phosgene/HCl ratios in the reaction step are required here. This process has the disadvantage that a variation of the parameters in the phosgenation is made difficult and the quality of the phosgenation is very sensitive as a result. In addition, the lack of flexibility in the parameters in the phosgenation makes the phosgenation very difficult to carry out in practice and requires a high engineering outlay.

Although processes of the type mentioned attempt to remove discoloring components at the correct point, they are not efficient enough, both because of their high engineering outlay or the high costs and also in terms of their color-lightening effect, since only slight degradation of color precursors occurs due to incomplete chemical reactions.

3. Addition of color-lightening additives to the crude isocyanate product obtained after the phosgenation and before the work-up EP-A 0 581 100 relates to a process for preparing polyisocyanates in which a chemical reducing agent is added after the phosgenation and before the removal of solvent, which according to this document likewise gives light-colored products.

According to U.S. Pat. No. 4,465,639, water is added to the crude product obtained after the phosgenation in order to lighten its color. EP-A 538 500, EP-A 0 445 602 and EP-A 0 467 125 describe the addition of carboxylic acids, alkanols or polyether polyols after the phosgenation for the same purpose.

Although the above-described methods of lightening the color are efficient, they have disadvantages in that the additives not only lighten the color but also undergo reactions with the isocyanates obtained as product, generally resulting, for example, in an undesirable reduction in the isocyanate content. In addition, there is the risk of formation of undesirable by-products in the MDI.

4. After-treatment of the end product

EP-A 0 133 538 describes the purification of isocyanates by extraction, giving fractions of a light-colored MDI.

EP-A 0 561 225 describes a process for preparing isocyanates or isocyanate mixtures which, according to this document, contain no color-imparting components, in which process the isocyanates obtained after the phosgenation of the corresponding amines are subjected to a hydrogen treatment at a pressure of from 1 to 150 bar and a temperature of from 100 to 180° C. According to the examples described there, isocyanate end products are hydrogenated as such or in the form of their solutions in suitable solvents.

These color-improving after-treatments of the isocyanate end products after complete removal of the solvent at elevated temperature are likewise not very efficient, since the high temperatures occurring during the work-up, in particular during the distillation of the solvent and (in the case of the preparation of polymeric MDI) the removal of monomeric MDI, have already resulted in the formation of stable colored substances which can be chemically degraded only with difficulty.

It is an object of the present invention to provide a new process for preparing isocyanates which contain no or only small amounts of color-imparting components. A further object of the invention is to provide a process for preparing isocyanates which, without the abovementioned treatment steps, leads to light-colored isocyanates which are suitable for producing polyurethanes or their precursors which have no color or only a slight color.

We have found that this object is achieved by preparing the isocyanates using phosgene which contains less than 50 ppm of bromine or bromine-containing compounds or iodine or iodine-containing compounds.

The present invention accordingly provides a process for preparing isocyanates by reacting an amine or a mixture of two or more amines with phosgene containing less than 50 ppm of bromine or iodine or their mixtures in molecular or bound form.

For the purposes of the present text, bromine or iodine in molecular form means molecules which consist entirely of bromine or iodine atoms. Bromine or iodine in bound form means molecules which comprise not only bromine or iodine but also atoms different from the specified atoms.

The phosgene used for the purposes of the present invention thus contains less than 50 ppm of bromine or bromine compounds or iodine or iodine compounds; or bromine and iodine; or bromine and iodine and bromine compounds; or iodine compounds and bromine and iodine; or bromine compounds and iodine compounds; or bromine and iodine and bromine compounds and iodine compounds.

The process of the present invention leads to isocyanates which, if desired even without the above-described additional treatments, can be used for preparing urethane compounds such as polyurethanes or their precursors which have no color or only a slight color.

The result obtained according to the present invention was particularly surprising because it had hitherto not been recognized that even extremely small traces of molecular or bound bromine or iodine or the abovementioned mixtures in the phosgene used for the preparation of isocyanates are sufficient to influence the product color in an undesirable way.

The phosgene used for the preparation of isocyanates generally has a certain content of molecular or bound bromine or iodine or the abovementioned mixtures. The content of bromine or iodine or such mixtures in the phosgene results from the chlorine used for preparing the phosgene, since the chlorine usually contains a certain proportion of bromine or iodine or both. The content of bromine or iodine or both in the chlorine generally results from the corresponding content in the salt used for producing the chlorine. However, it was previously not recognized that the bromine or BrCl present in the chlorine leads to formation of dibromophosgene or bromochlorophosgene in the phosgene synthesis (analogous to the formation of COBrF from CO+BrF$_3$; see W. Kwasnik in "Handbuch der präparativen anorganischen Chemie", editor: G. Brauer, Volume 1, 3$^{rd}$ Edition, Ferdinand Enke Verlag, Stuttgart, 1975, p. 224). These compounds are said to react similarly to phosgene with amines to form isocyanates and hydrogen bromide (U.S. Pat. No. 2,733,254). Analogous reactions may be assumed for iodine.

The phosgene having a low content of bromine or iodine or the abovementioned mixtures and used for the purposes of the present invention can be prepared in various ways known to those skilled in the art. One possible way of guaranteeing a low content of bromine or iodine or the abovementioned mixtures in the phosgene is, for example, the use of starting compounds which have a correspondingly low content of bromine or iodine or both in the preparation of the phosgene. In particular, the use of chlorine having an appropriately low content of bromine or iodine or both is a possibility here.

Methods of preparing suitable chlorine having a low content of bromine or iodine or both are known to those skilled in the art. In principle, the present invention can be carried out using any chlorine which meets the abovementioned specification, i.e. contains less than about 50 ppm of bromine or iodine or the abovementioned mixtures, for example 25 ppm or less. Thus, for example, it is possible to use chlorine which has been prepared by the electrolysis process or by the oxidation of HCl, for example by the Deacon process. U.S. Pat. No. 3,660,261 describes the preparation of chlorine having a particularly low bromine content by oxidative treatment of the salt used for the electrolysis. An alternative possibility is the removal of bromine or iodine or both from chlorine by means of distillation, selective condensation of the bromine or iodine in the stream of chlorine or by reactions with substances which react selectively with bromine or iodine or both, as described, for example, in JP 0075319. Naturally, it is also possible to use appropriate starting materials which contain essentially no bromine or iodine in the chlorine synthesis, e.g. essentially bromine- and iodine-free salt or bromine- and iodine-free HCl. Suitable processes are described, for example, in DE-A 18 00 844, DE-B 12 55 643 or DE-A1 197 26 530.

A further possible way of preparing low-bromine chlorine is described in Ullmann's Encyclopedia of Industrial Chemistry, 5$^{th}$ Edition, Volume A6, p. 463 and FIG. 70 on p. 465: when gaseous bromine-rich chlorine is subjected to a countercurrent scrub with liquid low-bromine chlorine, the chlorine gas to be purified is depleted in bromine and the liquid chlorine is enriched with bromine. To start up such a plant, the provision of a sufficient amount of low-bromine liquid chlorine is necessary; subsequently, a substream of the relatively low-bromine chlorine obtained can be liquefied and used for scrubbing the relatively bromine-rich chlorine. This process is carried out in columns containing customary internals which aid separation, for example trays, random packing or ordered packing. The achieved degree of depletion of bromine or iodine or both depends on the system pressure, the flow rates, the concentrations and the internals in the usual way for absorption and distillation processes; the design of the column given the desired degree of bromine depletion is therefore a purely routine task.

The largely bromine- and iodine-free chlorine obtained in this way can subsequently be converted into phosgene in customary and known processes as are described, for example, in Ullmanns Enzyklopädie der industriellen Chemie, 3$^{rd}$ Edition, Volume 13, pages 494–500.

A further way of obtaining phosgene having a low content of molecular or bound bromine or iodine or both is to remove molecular and bound bromine and iodine from the phosgene itself. Here too, it is once again possible in principle to use all customary separation methods, for example distillation, adsorption and the like. As far as the process of the present invention is concerned, the only important thing is to adhere to the abovementioned upper limit for the concentration of molecular or bound bromine or iodine or the abovementioned mixtures.

In a preferred embodiment of the invention, use is made of phosgene having a content of bromine or iodine or the abovementioned mixtures of less than 40 ppm, 35 ppm, 30 ppm or 25 ppm or less, in particular of 10 ppm or less.

The preparation of isocyanate taking place in the process of the present invention is carried out in a manner known to those skilled in the art by reacting an amine or a mixture of two or more amines with a super-stoichiometric amount of phosgene. It is in principle possible to employ all methods in which a primary amine or a mixture of two or more primary amines is reacted with phosgene to form one or more isocyanate groups.

In a preferred embodiment of the invention, the process of the present invention, i.e. the reaction of the amine or the mixture of two or more amines with the phosgene, is carried out in a solvent or a mixture of two or more solvents.

As solvent, it is possible to use all solvents suitable for the preparation of isocyanates. These are preferably inert aromatic, aliphatic or alicyclic hydrocarbons or their halogenated derivatives. Examples of such solvents are aromatic compounds such as monochlorobenzene or dichlorobenzene, for example o-dichlorobenzene, toluene, xylenes, naphthalene derivatives such as tetralin or decalin, alkanes having from about 5 to about 12 carbon atoms, e.g. hexane, heptane, octane, nonane or decane, cycloalkanes such as cyclohexane, inert esters and inert ethers such as ethyl acetate or butyl acetate, tetrahydrofuran, dioxane or diphenyl ether.

As amines, it is in principle possible to use all primary amines which can react appropriately with phosgene to give isocyanates. Suitable amines are, in principle, all linear or branched, saturated or unsaturated aliphatic or cycloaliphatic or aromatic primary monoamines or polyamines, provided that these can be converted into isocyanates by means of phosgene. Examples of suitable amines are 1,3-propylenediamine, 1,4-butylenediamine, 1,5-pentamethylenediamine, 1,6-hexamethylenediamine and the corresponding higher homologues of this series, isophoronediamine (IPDA), cyclohexyldiamine, cyclohexylamine, aniline, phenylenediamine, p-toluidine, 1,5-naphthylenediamine, 2,4- or 2,6-toluenediamine or a mixture thereof, 4,4'-, 2,4'- or 2,2'-diphenylmethanediamine or mixtures thereof and also higher molecular weight isomeric, oligomeric or polymeric derivatives of the abovementioned amines and polyamines. In a preferred embodiment of the present invention, the amine used is an amine of the diphenylmethanediamine series or a mixture of two or more such amines.

After going through the process of the present invention, the abovementioned compounds are in the form of the corresponding isocyanates, e.g. as hexamethylene 1,6-diisocyanate, isophorone diisocyanate, cyclohexyl isocyanate, cyclohexyl diisocyanate, phenyl isocyanate, phenylene diisocyanate, 4-tolyl isocyanate, naphthylene 1,5-diisocyanate, tolylene 2,4- or 2,6-diisocyanate or mixtures thereof, diphenylmethane 4,4'-, 2,4'- or 2,2'-diisocyanate or mixtures of two or more thereof, or else higher molecular weight oligomeric or polymeric derivatives of the abovementioned isocyanates or as mixtures of two or more of the abovementioned isocyanates or isocyanate mixtures.

In a preferred embodiment of the present invention, the amines used are the isomeric, primary diphenylmethanediamines (MDA) or their oligomeric or polymeric derivatives, i.e. the amines of the diphenylmethanediamine series. Diphenylmethanediamine, its oligomers or polymers are obtained, for example, by condensation of aniline with formaldehyde. Such oligoamines or polyamines or mixtures thereof are also used in a preferred embodiment of the invention.

The reaction of the low-bromine and low-iodine or even bromine-free and iodine-free phosgene which falls within the abovementioned restrictions and is to be used for the purposes of the present invention with one of the abovementioned amines or a mixture of two or more such amines can be carried out continuously or batchwise in one or more stages. If a single-stage reaction is carried out, this reaction preferably takes place at from about 60 to 200° C., for example at from about 130 to 180° C.

In a further embodiment of the invention, the reaction can, for example, be carried out in two stages. Here, in a first stage, the reaction of the phosgene with the amine or the mixture of two or more amines is carried out at from about 0 to about 130° C., for example from about 20 to about 110° C. or from about 40 to about 70° C., with a time of from about 1 minute to about 2 hours being allowed for the reaction between amine and phosgene. Subsequently, in a second stage, the temperature is increased to from about 60 to about 190° C., in particular from about 70 to 170° C., over a period of, for example, from about 1 minute to about 5 hours, preferably over a period of from about 1 minute to about 3 hours.

In a preferred embodiment of the invention, the reaction is carried out in two stages.

During the reaction, superatmospheric pressure can, in a further preferred embodiment of the invention, be applied, for example up to about 100 bar or less, preferably from about 1 bar to about 50 bar or from about 2 bar to about 25 bar or from about 3 bar to about 12 bar. However, the reaction can also be carried out under atmospheric pressure.

In a further preferred embodiment of the invention, the reaction is accordingly carried out at ambient pressure, generally about 1 bar. In a further preferred embodiment, the reaction can also be carried out at a pressure below ambient pressure.

Excess phosgene is preferably removed at from about 50 to 180° C. after the reaction. The removal of remaining traces of solvent is preferably carried out under reduced pressure, for example the pressure should be about 500 mbar or less, preferably less than 100 mbar. In general, the various components are separated off in the order of their boiling points; it is also possible to separate off mixtures of various components in a single process step.

The present invention further provides light-colored isocyanates as can be prepared by the process of the present invention.

The invention further provides for the use of isocyanates which can be prepared by the process of the present invention or by such a process for preparing urethane compounds, in particular polyurethanes. In a preferred embodiment of the invention, the isocyanates of the invention are used for producing polyurethane foams as are commercially available as, for example, rigid foams, semirigid foams, integral foams and flexible foams.

The invention is illustrated by the following examples.

In all examples, the bromine content in the phosgene was calculated from the bromine content of the chlorine used for the phosgene synthesis. The bromine content of the chlorine was determined by means of X-ray fluorescence analysis.

The viscosities reported in the examples were determined on a Lauda CD 20 viscometer at 25° C.

EXAMPLE 1

Preparation of the MDI Samples 100 g of polymeric MDA dissolved in 1.3 liters of monochlorobenzene are reacted under atmospheric pressure at 50–80° C. with 200 g of phosgene dissolved in 1.3 liters of monochlorobenzene in a 6 liter stirred reactor. The temperature is increased to about 120° C. over a period of 1–2 hours, during which time the reaction to form the isocyanates (125 g) takes place. Residual phosgene and monochlorobenzene are subsequently distilled off under gentle conditions (110° C., 100 mbar). The solvent-free crude MDI sample is subsequently after-treated for 45 minutes at 180° C. and a pressure of 10 mbar.

The phosgenations of Examples 1 to 3 were carried out under the same conditions. The experiments differed only in the bromine content of the phosgene.

EXAMPLE 1 a. Phosgene having a bromine content of less than 10 ppm was used for the synthesis.
b. Phosgene having a bromine content of 50 ppm was used for the synthesis.
c. Phosgene having a bromine content of 100 ppm was used for the synthesis.

The property data for the products are shown in Table 1.

Property data for the end products:

The property data for the isocyanate products prepared as Examples 1 to 3 were determined. In particular, the iodine color number customarily reported for MDI was determined. For this purpose, the samples (diluted 1:5 with monochlorobenzene) were measured on a photometer (from Dr. Lange, Berlin) in the program mode for the iodine color number.

TABLE 1

Property data for the examples

| | Bromine content of the phosgene (ppm) | $NCO^1$ (%) | $ICN^2$ |
|---|---|---|---|
| Example 1 | <10 | 32.2 | 18.9 |
| Example 2 | 50 | 32.2 | 24.1 |
| Example 3 | 100 | 32.3 | 28.6 |

[1] = NCO content (determined in accordance with ASTM D 5155)
[2] = iodine color number The results demonstrate a good lightening of the color of crude MDI when using low-bromine chlorine.

EXAMPLE 2

In an industrial process, 7.9 metric tons/h of crude MDA were reacted with 20.6 metric tons/h of phosgene in chlorobenzene as process solvent at 95° C. in a cascade of stirred vessels to form the isocyanate. The mixture leaving the phosgenation was freed of phosgene and chlorobenzene and after-treated thermally according to the prior art. Subsequently, some monomeric MDI was separated from the crude MDI obtained in this way, so that a polymeric MDI having a viscosity of about 200 mPas was obtained. The isocyanate property data were determined on this product (Table 2).

TABLE 2

Isocyanate property data for Example 2

| | Bromine content of the phosgene (ppm) | NCO (%) | ICN |
|---|---|---|---|
| Example 2a | 40 | 31.5 | 15 |
| Example 2b | 20 | 31.5 | 12 |
| Example 2c | 10 | 31.5 | 10 |

EXAMPLE 3

In an industrial process, 3.3 metric tons/h of crude MDA were reacted with 9.2 metric tons/h of phosgene in chlorobenzene as process solvent in a valve tray column at a bottom temperature of 110° C. to form the isocyanate. Excess phosgene and process solvent were subsequently distilled off at from 130 to 180° C. in a sequence of a plurality of distillation columns. The isocyanate property data were determined on this product (Table 3).

TABLE 3

Isocyanate property data for Example 3

| | Bromine content of the phosgene (ppm) | NCO (%) | ICN |
|---|---|---|---|
| Example 3a | 120 | 31.7 | 26 |
| Example 3b | 70 | 31.7 | 18 |
| Example 3c | 30 | 31.6 | 13 |

We claim:

1. A process for preparing isocyanates comprising the steps of providing a phosgene having a content of bromine or iodine or a mixture thereof in molecular or bound form of less than 50 ppm and reacting an amine or a mixture of two or more amines with said phosgene, thereby forming the isocyanates.

2. A process as claimed in claim 1, wherein the phosgene contains less than 25 ppm of bromine or iodine or mixtures thereof in molecular or bound form.

3. A process as claimed in claim 1, wherein the reaction is carried out in a solvent.

4. A process as claimed in claim 1, wherein the amine used is an amine of the diphenylmethanediamine series or a mixture thereof.

5. A process as claimed in claim 1, wherein the process is carried out in one or two stages.

6. A process as claimed in claim 1, wherein the reaction is carried out under super-atmospheric pressure or atmospheric pressure.

7. A process as claimed in claim 2, wherein the reaction is carried out in a solvent.

8. A process as claimed in claim 2, wherein the amine used is an amine of the diphenylmethanediamine series or a mixture thereof.

9. A process as claimed in claim 3, wherein the amine used is an amine of the diphenylmethanediamine series or a mixture thereof.

10. A process as claimed in claim 2, wherein the process is carried out in one or two stages.

11. A process as claimed in claim 3, wherein the process is carried out in one or two stages.

12. A process as claimed in claim 4, wherein the process is carried out in one or two stages.

13. A process as claimed in claim 2, wherein the reaction is carried out under super-atmospheric pressure or atmospheric pressure.

14. A process as claimed in claim 3, wherein the reaction is carried out under super-atmospheric or atmospheric pressure.

15. A process as claimed in claim 4, wherein the reaction is carried out under super-atmospheric pressure or atmospheric pressure.

16. A process as claimed in claim 5, wherein the reaction is carried out under super-atmospheric pressure or atmospheric pressure.

17. A process as claimed in claim 1, wherein isophorone diamine is reacted with said phosgene to form isophorone diisocyanate.

18. A process as claimed in claim 1, wherein 1,6-hexamethylenediamine is reacted with said phosgene to from hexamethylene-1,6-diisocyanate.

* * * * *